United States Patent [19]
Walters et al.

[11] Patent Number: 5,505,720
[45] Date of Patent: Apr. 9, 1996

[54] MELT BLOWN MENSTRUAL PAD FOR APPLICATION TO THE BODY

[75] Inventors: Bronwen L. Walters, Franklin Park; David Hujber, Mercerville, both of N.J.

[73] Assignee: McNeil-PPC, Inc., Milltown, N.J.

[21] Appl. No.: 296,996

[22] Filed: Aug. 26, 1994

Related U.S. Application Data

[63] Continuation of Ser. No. 981,899, Nov. 23, 1992, abandoned, which is a continuation of Ser. No. 713,944, Jun. 12, 1991, abandoned.

[51] Int. Cl.$^6$ .............................. A61F 13/15; A61F 13/20
[52] U.S. Cl. .......................... 604/378; 604/368; 604/358; 604/385.1
[58] Field of Search ...................... 128/888–889, 128/894; 602/41–46, 48–51, 58; 604/358, 359, 368, 369, 378–380, 382, 385.1

[56] References Cited

U.S. PATENT DOCUMENTS

| | | | |
|---|---|---|---|
| 2,331,355 | 10/1943 | Strongson | 604/385.1 |
| 3,670,731 | 6/1972 | Harmon | 604/368 |
| 4,041,951 | 8/1977 | Sanford | 604/380 |
| 4,318,408 | 3/1982 | Korpman . | |
| 4,360,021 | 11/1982 | Stima | 128/156 |
| 4,443,512 | 4/1984 | Delvaux | 604/379 |
| 4,578,070 | 3/1986 | Holtman | 604/379 |
| 4,798,603 | 1/1989 | Meyer et al. | 604/378 |
| 4,960,477 | 10/1990 | Mesek | 604/379 |
| 4,990,144 | 2/1991 | Blott | 128/156 |
| 5,175,046 | 12/1992 | Nguyen | 604/368 |
| 5,306,266 | 4/1994 | Freeland | 604/378 |
| 5,342,334 | 8/1994 | Thompson et al. | 604/378 |
| 5,352,217 | 10/1994 | Curro | 604/358 |
| 5,383,870 | 1/1995 | Takai et al. | 604/358 |
| 5,387,209 | 2/1995 | Yamamoto et al. | 604/358 |

FOREIGN PATENT DOCUMENTS

0383616A1  8/1990  European Pat. Off. .

*Primary Examiner*—Randall L. Green
*Assistant Examiner*—P. Zuttarelli
*Attorney, Agent, or Firm*—James P. Barr

[57] ABSTRACT

Improved pads for application to the body to absorb body fluids are disclosed. Menstrual pads having a plurality of projections which are most preferably filled with a superabsorbent material are disclosed, as well as methods for making same. The present invention discloses the use of novel melt-blown technology to form a surface having hollow projections which are then filled with superabsorbent. The present invention is directed to menstrual pads, as well as other pads which may be placed against the body, such as bandages. In the latter, medicinal compounds replace superabsorbents as the preferred material within the projections. In certain embodiments, a wicking layer, preferably comprised of peat moss based absorbent product is disposed between a cover layer and the projections containing superabsorbent.

13 Claims, 3 Drawing Sheets

FIG. 2
FIG. 3
FIG. 4
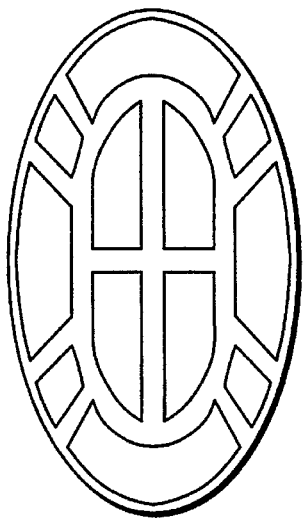
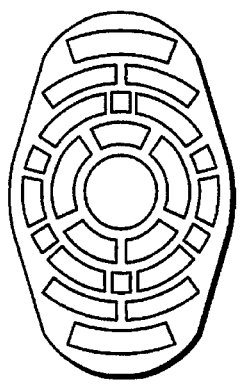
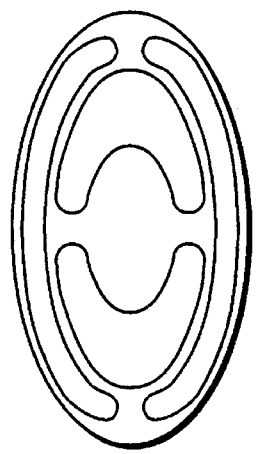
FIG. 5
FIG. 6
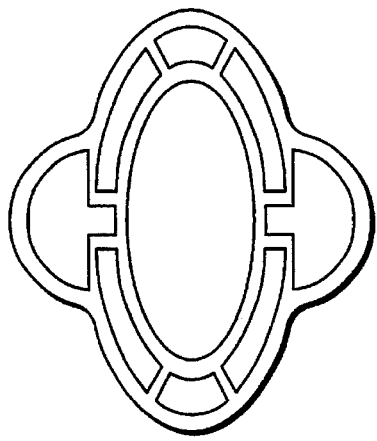
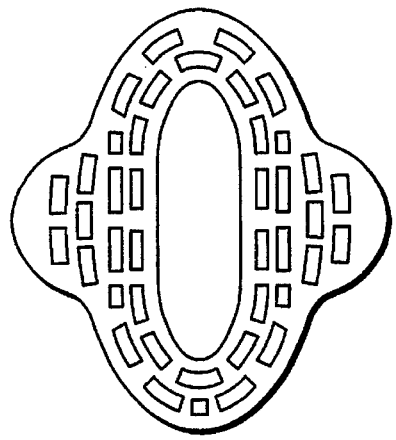

MELT BLOWN MENSTRUAL PAD FOR APPLICATION TO THE BODY

This application is a continuation of application Ser. No. 07/981,899 filed Nov. 23, 1992, now abandoned, which was a continuation of application Ser. No. 07/713,944 filed Jun. 12, 1991, now abandoned.

The present invention relates to absorbent products for application to the body. More particularly, it relates to absorbent pads which are used for feminine hygiene, such as menstrual or catamenial pads.

BACKGROUND OF THE INVENTION

In the field of menstrual pads, an unacceptable failure rate still exists with most products currently in use. Most pads cannot effectively absorb the overall amount of menstrual fluid exuded; moreover, they cannot absorb the fluid at the high flow rate encountered at certain times. Additionally, the absorbed fluid tends to remain at the point of collection. Improved distribution of menstrual fluid across the surface of the pad would therefore be desirable and would result in increased absorption by utilizing the full absorptive capacity of the materials within the pads.

Traditionally, menstrual pads have been made from fabric, pulp, and/or synthetic fibers, such as polypropylene, polyethylene, polyester, and other fibers. More recently, new higher absorbency products have been incorporated into these pads. One such absorbent is comprised of a thin layer of processed, compressed peat moss, which is scored to improve liquid penetration and absorbency, as described in U.S. patent application Ser. No. 851,270 of Mar. 13, 1992, which is assigned to the assignee of the present invention. However, peat moss board, while extremely high in capacity, is slow to absorb fluid and, therefore, napkins using peat moss board as an abosrbent, require additional means to aid in absorption.

Superabsorbents have also been used to increase the amount of liquid which is absorbed and retained by absorbent personal products. For example sodium carboxymethylcellulose (CMC) commercially available as AQUASORB/AS50 from the Aqualon Company of Wilmington, Del., USA is frequently used in personal care applications for absorbing and retaining blood, saline or other body fluids. Superabsorbents typically absorb from 5 to 10 times their dry weight of water, although somewhat less by weight of menstrual fluid, which is absorbed at a relatively lower rate. While superabsorbents have certain advantages, they tend to form a gel as they absorb fluid. The gel prevents fluid from flowing deeper into the superabsorbent layer. This phenomenon is known as "gel-blocking". Gel-blocking occurs because as fluid encounters a quantity of superabsorbent, the first portion of the superabsorbent to contact the liquid being absorbed turns into a gel. Because superabsorbents tightly bind liquid once it has been absorbed, they cause other efficiency decreasing effects. As absorption occurs, the superabsorbent swells considerably; normally, superabsorbent powders are distributed within a fibrous matrix, such that the swelling is accommodated through a compression of the surrounding fibers. If the surrounding fibers are already near saturation, the swelling of the superabsorbent may not result in as much of an increase in absorptive capacity as would be expected. It is important, however, to overcome these phenomena and achieve maximum efficiencies when using superabsorbents, since they are more expensive on a per weight basis than any other component of a typical absorbent product.

Thus, a need still exists for a comfortable menstrual pad which rapidly absorbs fluid and retains that fluid for extended periods of time without leaking. It would therefore be desirable to be able to incorporate superabsorbents and/or the improved absorbent peat moss products described above into an absorbent pad while making maximum efficient use of the absorbent properties of those materials.

SUMMARY OF THE INVENTION

A novel menstrual pad is provided which comprises a structural layer defining an array of body-surface directed projections, each of which defines a cavity. These cavities preferably contain material of differential absorbency, such as a superabsorbent. The distribution of these projections on the structural layer helps to direct the flow of the menstrual fluid across the surface of the pad by creating numerous intersecting channels along its body facing surface.

This array also presents a substantially greater surface area for fluid absorption and transmission than those products of the prior art.

In a preferred embodiment the generally tapered shape of these projections leads to excellent transmission of fluid away from the body surface, this transmission is enhanced by a "pumping action" of each projection as the result of body movement. When superabsorbent is disposed in the cavities of the structural layer, the problem of gel-blocking is substantially reduced because the discreet array of sections superabsorbent material substantially prevents a gel-block from occurring by exposing the superabsorbent material to fluid from nearly all directions.

In a most preferred embodiment of the present invention, a hydrophilic backing layer is disposed under the structural layer. This layer acts as a wicking layer and extends under both the above-mentioned channels, and across the open cavity backs defined in the structural layer. Preferably, the wicking layer is a combination of pulp fiber and superabsorbent. The wicking layer may also be a compressed pulp layer. Alternatively, the wicking layer may be a processed compressed peat moss layer. The wicking layer should readily absorb liquid that is transmitted through the structural layer and through the base of the channels, which in turn can transmit that liquid across and into the superabsorbent material located within the cavities. This wicking layer may also be composed of compressed peat moss board. As the pad is compressed due to routine body movements, the menstrual fluid in the wicking layer will be transferred to the superabsorbent, where it will be retained as a gel.

The present invention thus provides a menstrual pad having a fibrous structural layer defining an array of body surface directed projections, each projection defining a cavity region. In a preferred embodiment, a backing layer is disposed over at least the cavity regions thereby defining cavities between the structural layer and the backing layer. Additional facing layers may optionally be provided to soften the product and to provide evenness across the face of the pad.

This invention also relates to methods of making the products of this invention. The absorbent products of the present invention may be fabricated using air-laid pulp technology, transerse webber, technology or melt-blown technology. In general, any means of forming fibers, molding said fibers into a pad shape and heating them known to those of skill in the art may be used to make the products of this invention.

The methods of the present invention comprise the steps of providing a positive mold having a plurality of projections defining the shape of cavities to be formed in the pad. A layer of synthetic fiber forming material is then meltblown over the mold to form a structural layer defining a plurality of cavities corresponding to the projections of the mold. A backing layer is then applied to the structural layer to form a menstrual pad. In a most preferred embodiment of the methods disclosed, prior to the blowing step, synthetic fiber forming material is heated until molten, at a temperature which does not exceed its crystalline melt point. The melt blowing is therefore conducted under conditions wherein the molten fibers have not completely solidified until after they have contacted the mold. As a result, additional structural integrity is provided to each projection by the increased adherence of adjacent fibers to each other as they cool to form the walls and ends of the projections.

Another means for making the products of this invention uses an apparatus known as a "transverse webber". This apparatus and process for using it is described, for example, in European published Patent Application No. 90 301685.5, published Aug. 27, 1990. In order to make the products of this invention, a thermosetting polymer, such as urethane or silicone, is cast into a mold from a machined replication of cells. Thermoplastic cover fibers are laid down in the mold, outlining and partially filling the cavities of the mold. Thermoplastic fibers of the resilient wicking layer are placed on top of the cover fibers and fill the remaining volume of the cells. The next layer laid down on the molded web is an absorbent core layer, which may contain pulp, pulp board or a combination of pulp and superabsorbent. The resulting composite molded web is through-air bonded to cause the thermplastic fibers to be stabilized in position. A stream of air is then forced through the web to separate it from the mold. A barrier layer such as repellent pulp with sealant or lower polyalkylene material is then attached to the pad and placement adhesive and release paper applied. The product may then be die-cut and is ready for packaging.

It is thus one object of this invention to provide an improved absorbent pad for use against a user's body which comprises an array of body-directed projections, each of which comprises hollow cavities for retaining a material of substantially higher adsorbents.

It is another object of the present invention to provide a novel method of melt blowing absorbent products to achieve the above-described structure. These and other objects of the present invention will become apparent from the following, more detailed description.

BRIEF DESCRIPTION OF THE DRAWINGS

FIGS. 2–6 are plan views of absorbent pad designs made in accordance with the present invention.

DETAILED DESCRIPTION OF THE PREFERRED EMBODIMENTS

Figure 1:
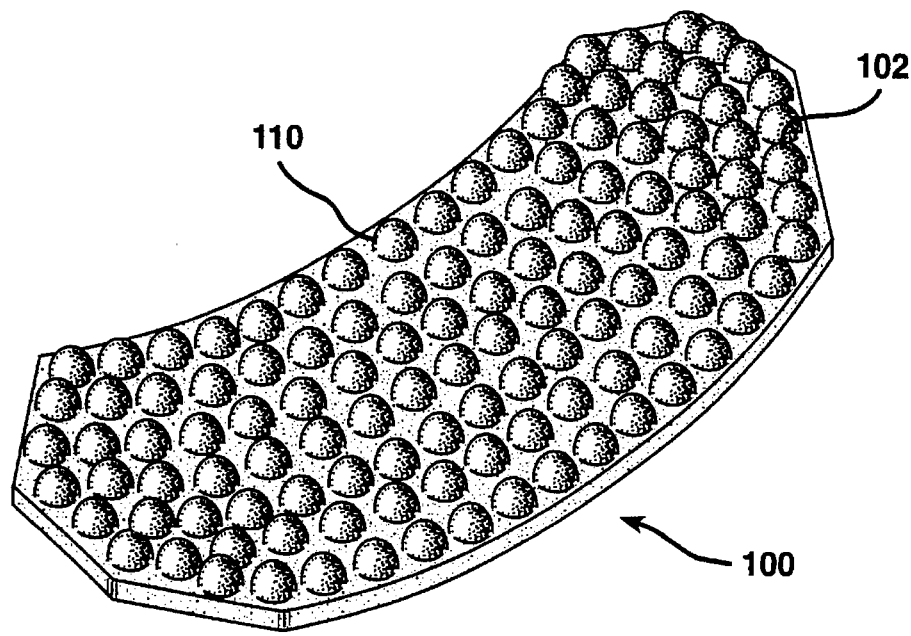
FIG. 1 is a perspective view of a menstrual pad made in accordance with the present invention.

Referring to FIG. 1, a menstrual pad 100 made in accordance with the present invention is shown in a perspective view. A structural layer 102 forms the body facing side of the pad. In some embodiments further layers will overlie the structural layer to provide pads having a softer "feel" or other properties. The structural layer 102 is comprised of an array of body-surface directed projections 110. Each projection 110 defines a cavity which, as explained below, may be filled with a material having a differential absorbency or other property.

Depending upon the properties desired and the composition of the absorbent product, numerous variations in the layout of the projections of the structural layer 102 depicted in FIG. 1 are contemplated by the present invention. As shown in FIGS. 2–6, plan views of an outline of a typical catamenial pad can be filled with a variety of geometric shapes, representing projections containing superabsorbents or other materials. In FIG. 2, an oval pad is provided with segmented projections about its periphery and a central projection equally divided in four portions by 90% center lines. A variation containing a greater number of projections is shown in FIG. 3. Alternately, in certain applications, it may be desirable to maintain larger, more continuous projections, as shown by FIG. 4. As known to those familiar with the design of absorbent products, certain designs possess "wings" or "flaps" comprised of lateral extensions from the central pad. As shown in FIGS. 5 and 6, either a single large projection or a series of segmented projections can be incorporated into the design of the face of the pad depending upon the distribution desired.

Figure 7:
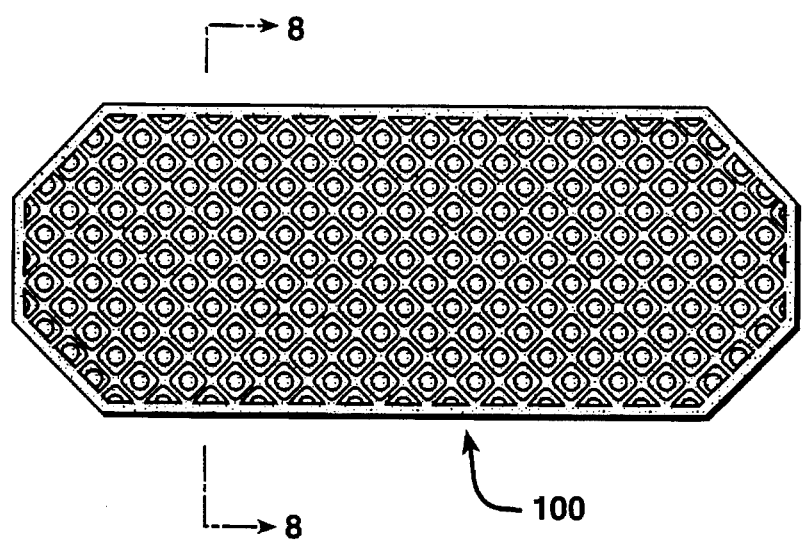
FIG. 7 is a plan view of the menstrual pad of FIG. 1.
Figure 8:
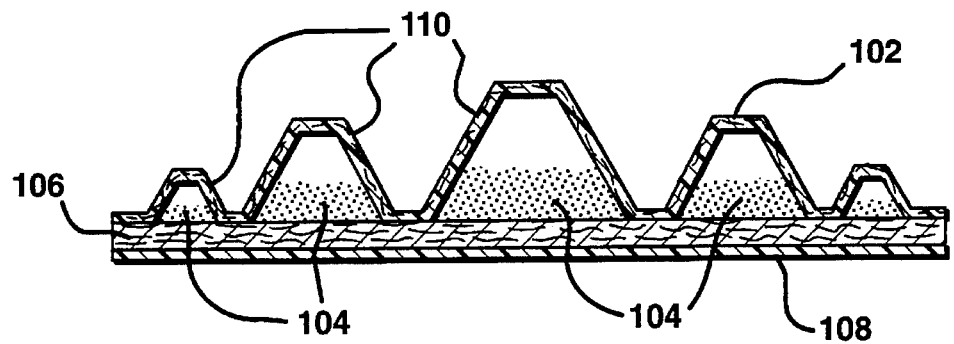
FIG. 8 is a cross-sectional view of a menstrual pad similar to that shown in FIG. 7 taken along line 8—8.

Referring now to FIG. 7, a plan view of a preferred embodiment of the present invention similar to the pad depicted in FIG. 1 is shown. The pad 100 is generally rectangular, however, the corners have been eliminated to result in an elongated octagonal shape. As depicted in FIG. 8, the embodiment depicted in FIG. 7 differs from that of FIG. 1 in that the body surface directed projections 110 are of unequal height. As shown in FIG. 8, the projections near the longitudinal centerline of the pad are preferably of relatively greater height in comparison with those along the periphery. As will be realized by one or ordinary skill, variations in projection height both longitudinally and laterally permit a vast number of surface configurations to be obtained. Similarly, the height of the projections depicted in FIGS. 2–6 can also be varied to provide a more comfortable and conformal surface.

As depicted in FIG. 8, the first, body-surface facing layer is the structural layer 102. The structural layer 102 of this present invention is most preferably constructed utilizing a novel melt-blown process, as disclosed herein. The meltblown process preferably used in the present invention involves extruding fibers in accordance with U.S. Pat. No. 4,318,408— Korpman and casting the fibers onto a positive mold. The process of this invention requires fibrous strands of material to be "blown" onto a positive mold.

In order to construct the pads of this invention, polymeric materials are fed into a nozzle or orifice which blows molten fibrous strands onto a positive mold as the nozzle or orifice passes across the mold. The distance from the molds determines whether the fibers are still molten when they strike the surface of the mold or whether they have cooled sufficiently and to form a softer layer when they are deposited upon the mold surface or on the fibrous layers already formed on the mold surface.

In one embodiment, for example, three different passes are made in order to create the structural layer 102, as shown in FIG. 8, the distance from the tip of nozzle to the mold surface was 2.0, 12.0 and 18.0 inches (5.08, 30.48 and 45.72 cm) respectively. The first pass, at 2.0 inches (5.08 cm), creates fairly rigid cavities, and the remaining passes become increasingly soft, so that a soft body-facing surface is created while the interior of the cavities is relatively rigid. As will be understood by one of ordinary skill, the temperature at which the polymer is blown, the distance, and the characteristics of the resulting layer are dependent upon the nature of the polymer used. When used for containing an absorbent, it is important that the resulting structure not fracture when the product is subjected to its intended use. The types of polymers that can be used in the process of the present invention may be either hydrophilic or hydrophobic. In preferred embodiments, polyethylene or polypropylene are used, however, other types of polymers can be substituted or different polymers may be laid in alternate layers.

Referring again to FIG. 8, a second material 104 preferably deposited within the structural layer 102 subsequent to the deposition of structural layer 102. Preferably, the second material 104 contains a superabsorbent material which substantially fills the cavities. Thus, a cavity is made upon each of the projections of a mold, the mold is removed and the cavities are preferably subsequently filled with a superabsorbent material. In a preferred embodiment, the superabsorbent material which is filled within the cavity is in the powdered form and is preferably sprayed on after the structural layer 102 is formed and the mold removed. The powdered superabsorbent preferably fills between about 3% and about 80% of the cavity. In a most preferred embodiment, between about 10% and about 30% of the cavity is filled.

The shape of the projection which is filled with superabsorbent material will depend upon the nature of the superabsorbent material selected, and the relative transmission rates directly through the cavity wall. For example, the superabsorbent AQUASORB/A 250 which is a sodium carboxymethyl cellulose (CMC)-based mixture available from the Aqualon Company of Wilmington, Del., as described above, provides good results. As shown in FIG. 8, the cross-section of a preferred projection is trapezoidal, the shape of the projection being in the form of either a truncated cone or truncated square pyramid. Preferably, the angle of the apex of the projection ranges from about 1.0 to 60.0 degrees, thereby permitting a wide range of configurations. As readily understood by those of ordinary skill, however, numerous other geometric shapes may be used for the projections.

As pointed out above, the projections may be substantially uniform in height across the surface of the pad. However, in certain embodiments, such as that shown in FIG. 8, it may be desirable to vary the height of the projections in different regions of the pad. This will permit further improvements and refinements in the flow distribution and absorbency in the overall pad. For example, a "mound" of relatively higher projections can be formed in the central region of the pad to increase the absorptive capacity in the region most likely to encounter the highest flow. Thus, in the plan views depicted in FIGS. 2–7, either the central segments or the edge portion segments could be varied in height relative to the other segments. Also, although the projections may cover the entire body facing surface of the pad, covering between about 30% and about 80% of the overall surface area with projections provides good results. The coverage may be either continuous or discontinuous, as shown, for example, by FIGS. 1–7.

Referring again to FIG. 8, in a most preferred embodiment, each cavity underlying a projection 110 is preferably closed by a hydrophilic backing layer 106. In order to provide a complete absorbent product a hydrophobic facing layer 108 may also be provided. The garment side hydrophobic facing layer 108 overlies the absorbent backing layer 106. However, as will be readily understood by those of ordinary skill, not all embodiments of the present invention will comprise a backing layer 106. In certain embodiments, the facing layer 108 will overlie the structural layer 102 and the superabsorbent or other material disposed thereon. Such an embodiment may be preferred where the additional absorptive capacity provided by the backing layer 106 is unnecessary and less bulk is desirable, such as in a panty shield.

Figure 9:
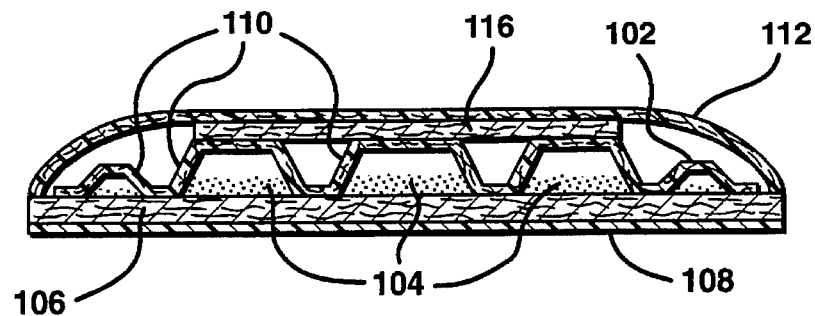
FIG. 9 is a cross-section of another embodiment of an absorbent pad made in accordance with the present invention.

As pointed out above, making full and efficient use of compressed peat moss materials in absorbent products is difficult. As shown in FIG. 9, the present invention provides a solution to this problem. The cross-section depicted is substantially similar to that depicted in FIG. 8, however, the projections 110 of the structural layer 102 are of substantially uniform height in the central region of the pad. In this embodiment of the present invention, however, a layer of peat moss-based absorbent material 116 can be applied to the body facing side of the projections. The inclusion of this layer of the peat moss material 116 has the additional advantage of utilizing the advantageous absorbent properties of the powdered superabsorbent 104 preferably placed in the cavities 110 within the structural layer. The peat moss product layer 116 absorbs and quickly wicks up exuded fluids. Peat moss products, however, express fluid easily under compression, permitting the superabsorbent to absorb the liquid from the compressed peat moss product and retain it. Thus, the combination of a superabsorbent and a peat moss product as set forth herein provides an optimal use of the absorbing characteristics of both products. A polymer cover 112 is also provided to overlie the peat moss product 116 and any remaining uncovered projections 110. This cover can be designed to provide a dry "feel" to the body facing surface of the pad as is known to those of ordinary skill in the art.

Figure 10:
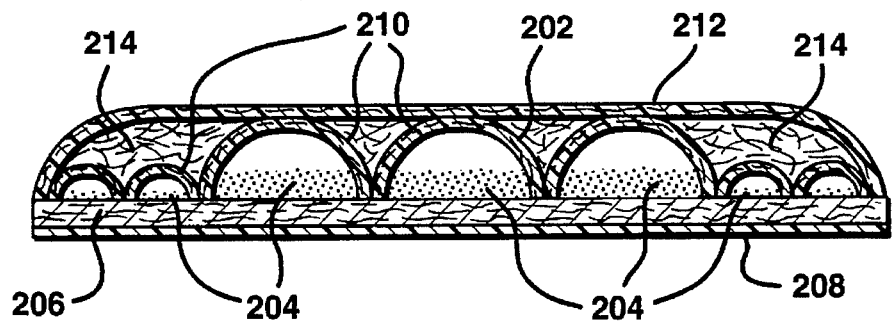
FIG. 10 is a cross-section of another embodiment of an absorbent pad made in accordance with the present invention.

Referring now to FIG. 10 an alternative construction of an absorbent pad made in accordance with the present invention is shown. In this embodiment a structural layer 202 is again formed as set forth above, preferably using the melt-blown technique disclosed. As shown in cross-section, the cavities 210 of the structural layer 202 are substantially arcuate-shaped, although other shapes may be substituted, such as the trapezoidal cross-section disclosed above. In the embodiment of FIG. 10, it can be seen that the cavities 210 are less than fully filled with a powdered superabsorbent material 204 or other filler. This design permits the superabsorbent to expand to fill the cavities as fluid is absorbed.

Referring still to FIG. 10, it can be seen that overlying the structural layer 204 is a core 214 comprised of pulp or other absorbent material. As discussed above with reference to the peat moss/superabsorbent composite absorbent products disclosed in FIG. 9, the composite structure disclosed in FIG. 10 makes full and efficient use of the absorbent cross-flow and wicking characteristics of the pulp core 214, while providing an efficient avenue for excess fluid absorption and retention in the form of the superabsorbent 204 disposed within the cavities 210 of the structural layer 202.

In the embodiment of FIG. 10 in particular, alternative preferred fillers which may be placed within the cavities depicted include medicaments, which might be used when pads made in accordance with this embodiment of the present invention are used as wound dressings. The wicking characteristics of the pulp core 214 also add to the effectiveness of the absorbent product in the instance where a medicament is substituted for superabsorbent 204. Specifically, the pulp core 214 permits the medicament retained in the cavities 210 to spread readily over the entire surface of the pad, thereby producing a more even and effective distribution.

Finally, in certain embodiments such as that shown in FIG. 10, a polymer cover 112,212 or other surface layer may be provided to enhance the effectiveness of the absorbent pad. For example, a facing sheet 112,212 may be provided on the body facing side of a catamenial pad made in accordance with the present invention. Since the superabsorbent preferably provided will draw the absorbed fluid through the absorbent core and retain it, a dry and comfortable surface will be presented to the user's body.

In other embodiments, however, the facing layer 108 serves as a garment facing surface which also preferably remains clean and dry. The facing layer 108 is intended to prevent any absorbed fluid not trapped within the cavities or absorbed by the backing layer 106 from contacting the garment to which the absorbent product is attached.

Useful products utilizing the products of this invention may be made by filling the cavities with medicinal compounds, such as antibacterial medication, disinfectant or other medicaments. As will be understood by those of ordinary skill, the cavities described and disclosed above need not be of any particular size. In applications relating to the application of medicine, relatively small microcavities are formed and two medicines, a first for cleansing a wound to get rid of impurities, and a second antibacterial medication would preferably be provided. Thus, the second layer of material 104 depicted in FIG. 2 would be either a composite layer or a mixture of two medicinal compounds. In a bandage, the cavities would thus carry a complete wound healing system. In certain applications, it may also be desirable to take advantage of the properties of the cavities formed by the novel process of the present invention by creating a structure which would release other medications. This may be accomplished by intentionally promoting the fracture of the cavities upon use. As set forth above, by regulating the temperature, distance and other parameters surrounding the polymer deposition step of the process of the present invention a structure having particular physical characteristics may be obtained. Therefore, when desired, a structural layer may be made of a polymer which has been heated beyond its crystalline melt point, resulting in a brittle and/or fragile surface.

Finally, in certain other embodiments it may be desirable to leave unfilled the cavities formed by the methods of the present invention. It has been found that consumers believe that thicker absorbent products are more effective. Thus there is a perceived need to provide absorbent products which are thicker than the amount of absorbent material contained therein warrants. Such an embodiment might be comprised of the structural layer 102 and the facing layer 108, other absorbents or absorbent layers may or may not be included. The present invention thus permits the packaging of "air" into the product. While this embodiment does not take full advantage of the numerous advantages described above in relation to the process and product of the present invention such an embodiment may nonetheless be found useful and advantageous in certain circumstances.

EXAMPLE I

Four versions of sample material made in accordance with the present invention were formed as follows:

Cover Fiber: 1050 3 d×1.5
Resilient/Transparent Layer
65% Fiber 1: D-331 (commercially available from E.I. dupont de Nemours Company, Wilmington, Del.) 5.5 d× 1.5"
35% Fiber 2: D-270 (commercially available from E.I. dupont de Nemours Company, Wilmington, Del.) 4 d× 1.5
Pulp Binder Layer
65% Fiber 1: D-331 5.5 d×1.5"
35% Fiber 2: D-270 4 d×1.5"
Pulp Layer: IP Supersoft ELM cellulose wood pulp
The samples were formed as follows:
D-331 and D-270 are polyester fibers available from E.I. DuPont Company of Wilmington, Del. IP Supersoft ELM pulp is cellulose wood pulp.

TABLE 1

| SAMPLE I.D. | RESILIENT/TRANSPARENT TARGET(g/pad) | TOTAL TARGET(g/pad) |
|---|---|---|
| S1 | .450 | 4.85 |
| S2 | .250 | 4.65 |
| S3 | .450 | 4.75 |
| S4 | .250 | 4.55 |

The products were then tested against an interim Stayfree/ Maxi Pad using Synthetic Protein Test Fluid. All products tested comprised a compressed pulp layer; the results obtained are set forth in Table 2:

TABLE 2

| Sample | | Strikethrough (sec) | Stain Area (sq in) | Strikeback (grams) |
|---|---|---|---|---|
| S1 | Avg. | 37.20 | 2.28 | .32 |
| | Std. | 5.04 | .12 | .07 |
| S2 | Avg. | 41.20 | 2.36 | .33 |
| | Std. | 2.56 | .28 | .08 |
| S3 | Avg. | 35.00 | 2.30 | .37 |
| | Std. | 3.16 | .05 | .06 |
| S4 | Avg. | 39.40 | 2.33 | .39 |
| | Std. | 3.61 | .22 | .05 |
| Stay- free/ | Avg. | 227.40 | 3.54 | .22 |
| | Std. | 35.09 | .10 | .02 |

The results set forth in Table 2 demonstrate that the absorbent products of the present invention allow the fluid being absorbed to move through the cover layer at a faster rate than the Stayfree™ products. Also, the samples of the present invention contained a smaller total stain area than the other product. As seen in Table 1, the products of the present invention exhibited a higher strikeback time than the other products. However, when the test was repeated using Synthetic Physiological Napkin Test Fluid, the Stayfree™ product exhibited a strikeback value of 2.10 g, while sample S3 of the present invention had a strikeback value of 0.22 g.

In-vitro testing was also performed comparing the same samples against the Stayfree™ product. All products were tested without a compressed pulp layer in a 1.0% saline solution. The results of this test are set forth in Table 3.

Clearly, the equilibrium capacity of the products made in accordance with the present invention is larger than that of the pulp-based Stayfree™ brand maxipad product. A comparison of the rate to maximum capacity results indicates that the products of the present invention absorb fluid at a faster rate. The data in Table 3 also indicate that the structure of the present invention exhibits a greater resistance to wet collapse and a greater wet recovery than the other product.

Although the pulp-based Stayfree™ product retained a larger percentage of the fluid absorbed during the 0.07 psi. cycle, the actual amount of fluid contained in the structure of the products of the present invention during the second 0.50 psi cycle was larger.

Although certain embodiments of the present invention have been set forth with particularity, the present invention is not so limited. Accordingly reference should be made to the appended claims in order to determine the scope of the invention.

We claim:

1. A menstrual pad for absorbing body fluids comprising:
   a) a structural layer comprised of a polymeric material defining an array of preformed, self-supporting body-surface directed productions, each projection formed by a wall having a thickness and having an outer surface corresponding to a body facing surface and an inner surface defining a cavity region, the rigidity of said wall varying across said thickness thereof, and wherein the inner surface of said wall is more rigid than the outer surface of said wall; and
   b) a fluid transport layer disposed at least over said cavity regions to define cavities between the structural layer and said fluid transport layer.

2. The pad of claim 1, wherein absorbent material is disposed within at least one of said cavities defined between the structural layer and the fluid transport layer.

3. The pad of claim 2, wherein said absorbent material fills between 3% and 80% of the volume of said cavities.

4. The pad of claim 3, wherein said absorbent material fills between 10% to 30% of the volume of said cavities.

5. The pad of claim 1, wherein said pad further comprises a hydrophilic wicking layer disposed between said structural layer and said fluid transport layer.

6. The pad of claim 5, wherein the wicking layer comprises compressed peat moss.

7. The pad of claim 1 wherein the fluid transport layer is comprised of a hydrophobic material.

8. The pad of claim 2, wherein said absorbent material comprises a polymeric superabsorbent material for absorbing liquids and retaining the liquids in a gel.

9. The pad of claim 1 wherein the projections are substantially uniform in height.

10. The pad of claim 1 wherein said projections are generally of varying height in different regions of the pad.

11. The pad of claim 10, wherein the pad has a central region, and wherein a portion of the projections of varying height generally form a mound in the central region of the pad.

12. The pad of claim 1, further comprising material disposed in each of said cavities and a first layer disposed above said projections, said first layer being fluid pervious, and wherein said projections are sufficiently rigid to support said first layer without resting on said material.

13. The pad of claim 12, further comprising a second layer disposed above said projections, said second layer being formed from peat moss, and wherein said projections are sufficiently rigid to support said second layer as well as said first layer without resting on said material.

* * * * *